United States Patent [19]

Russell

[11] Patent Number: 4,582,794

[45] Date of Patent: Apr. 15, 1986

[54] METHOD OF DETERMINING POLYAMINE CONTENT OF BIOLOGICAL FLUIDS

[75] Inventor: Diane H. Russell, Tucson, Ariz.

[73] Assignee: The University of Arizona Foundation, Tucson, Ariz.

[21] Appl. No.: 418,247

[22] Filed: Sep. 15, 1982

[51] Int. Cl.[4] .............................................. C12Q 1/52
[52] U.S. Cl. ....................................... 435/16; 435/803
[58] Field of Search ............................. 435/4, 16, 803

[56] References Cited

FOREIGN PATENT DOCUMENTS 55-35208  3/1980  Japan ...................................... 435/4

OTHER PUBLICATIONS

Haddox et al., P.N.A.S. USA, 78(3):1712–1716 (Mar. 1981).

Primary Examiner—Esther M. Kepplinger
Attorney, Agent, or Firm—Mason, Kolehmainen, Rathburn & Wyss

[57] ABSTRACT

This application describes a method of determining the amount of organic polyamine in an aqueous solution to be assayed, which comprises (1) incubating a measured volume of said solution with a solution containing a protein with glutamine residues and a small, known amount of radiolabeled polyamine, in the presence of transglutaminase, (2) placing aliquots of the incubated solution on thin layer chromatographic strips treated with aqueous acid, (3) treating said strips with dilute aqueous acid solution to cause ascending chromatography, (4) cutting from the strips the sections where the aliquots had been applied thereto, (5) counting the radioactive scintillations of said sections, (6) carrying out steps (1) through (5) with the same volume of a standard solution containing a known amount of said polyamine, and (7) calculating the amount of polyamine in the solution to be assayed from the scintillation count made in the test procedure thereon in comparison to the scintillation count made in the test procedure conducted on the standard solution containing the known amount of said polyamine.

13 Claims, 3 Drawing Figures

METHOD OF DETERMINING POLYAMINE CONTENT OF BIOLOGICAL FLUIDS

This invention relates to a method of determining the amounts of polyamines in biological fluids. More particularly it relates to a procedure for analyzing body and tissue fluids and determining the amounts of polyamines therein as part of a program for detecting changes in body chemistry relevant to certain degenerative diseases.

BACKGROUND OF THE INVENTION

Certain polyamines, such as putrescine, spermidine and spermine, have been established as biochemical markers or indicators of normal and pathological growth. In malignancy, the urinary concentrations of spermidine reflect the tumor cell loss and the urinary level of putrescine is related both to the number of tumor cells in cell cycle and to the tumor cell loss factor. A greater than two-fold increase in urinary spermidine within 72 hours of chemotherapy predicts a complete or a partial response with a high degree of accuracy. Urinary putrescine titre may be valuable not only in assessing the early response to therapy but also in determining whether the chemotherapy promotes a later burst of cell proliferation. Erythrocyte spermidine concentrations also appear to track alterations in tumor kinetics. Alterations in intracellular and extracellular polyamines in other pathologies such as psoriasis, muscular dystrophy and cystic fibrosis also accurately reflect the disease activity and, in those cases studied, response to therapy.

Therefore, the determination of polyamine concentrations in extracellular fluids and in erythrocytes allows for (1) the early assessment of response to multimodality therapy, (2) disease or tumor staging, and (3) assessment of disease activity including long-term monitoring of polyamine concentrations to pinpoint remission and relapse in adjuvant patients. Information obtained by the monitoring of polyamines could result in prolongation of survival time of patients as well as assist in the design of the most effective therapy regimen for the pathology. Since other such specific kinetic markers are not available, polyamines can be clinically utilized to track tumor evolution and tumor response to therapy in those patients at high risk in which such measurements could be translated into therapeutic efficacy.

The polyamines, putrescine, spermidine and spermine, are ubiquitous components of both procaryotic and eucaryotic cells. They function as the organic cations of the cells and serve roles in protein and nucleic acid synthesis, structure and function. Polyamines also are found in the extracellular fluids in mammalian organisms. Their levels in plasma, urine and cerebrospinal fluid are useful indicators of disease activity, specifically with relation to neoplasia, and are of predictive value in assessing the efficacy of treatment and the maintenance of remission.

Elevated levels of putrescine, spermidine and/or spermine have proven to be indicators of pathology in cancer, cystic fibrosis, psoriasis and Duchenne muscular dystrophy (DMD). Further, an increased excretion of spermidine (greater than two-fold of control level prior to therapy) prescribes a partial or complete response to therapy with a high degree (greater than 95%) of accuracy.

Current sensitive methods for estimating polyamines, accurate to the pmole level, utilize either high-pressure liquid chromatography, which requires an initial large monetary investment in equipment and is limited in the number of samples which can be analyzed in one day, or a purified specific antibody. The ability of the enzyme transglutaminase to incorporate the polyamines into a covalent isopeptide linkage with glutamine residues on protein substrates provides a novel means for estimating polyamine levels in tissue or biological fluid samples. This application presents the details of a radioenzymatic method, sensitive to the pmole level, for rapidly and simply measuring polyamines.

OBJECTS OF THE INVENTION

It is an object of this invention to provide a simple, rapid and accurate method of determining the levels of plasma and urinary polyamines. More particularly it is an object to provide a procedure for determining the levels of putrescine, spermidine, cadaverine and spermine in body fluids and tissues. It is a further object to provide an analytical kit for carrying out such determinations. These and other objects are apparent from and are achieved in accordance with the following disclosure.

GENERAL DESCRIPTION OF THE INVENTION

Figure 3:
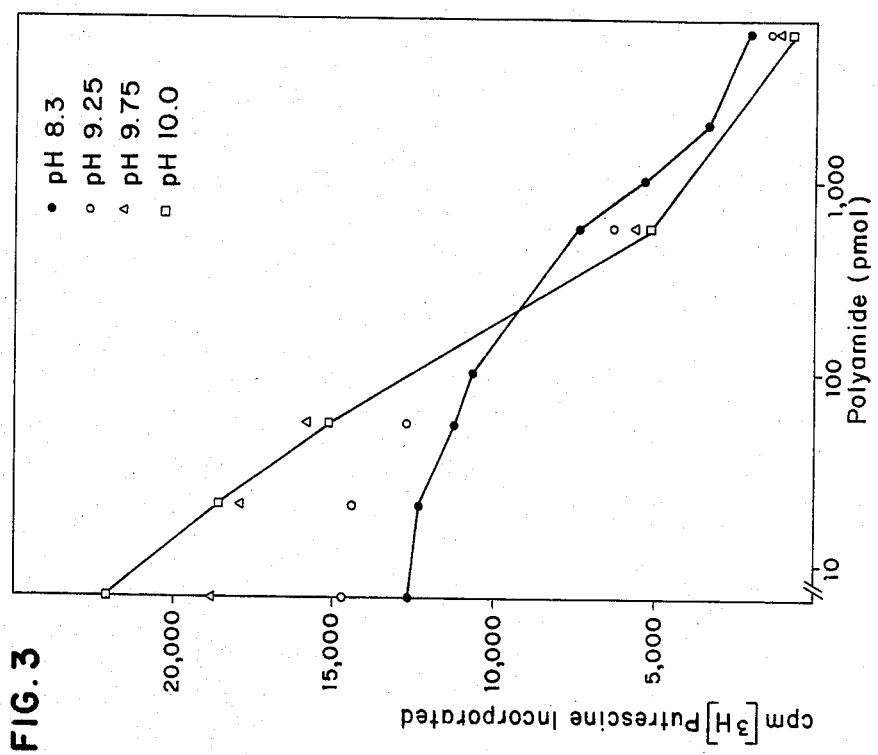
FIG. 3 illustrates the pH-dependence of the transglutaminase reaction. The transglutaminase competition assay was conducted in the presence of 30 mM tris(hydroxymethyl)aminomethane HCl, pH 8.3 (closed circles); 30 mM glycine, pH 9.25, (open circles); 30 mM glycine, pH 9.75 (open triangles); or 30 mM glycine, pH 10.0 (open squares). The data were obtained in the presence of increasing amounts of unlabeled putrescine. Similar results were obtained with spermidine or spermine.

The invention is based on the ability of transglutaminases, enzymes that occur in a wide variety of cell types, to conjugate polyamines to proteins such as casein. Any [$^3$H]- or [$^{14}$C]-polyamine can be used to label the reaction. The total pool of polyamines is assayed by the amount of radiolabeled polyamine incorporated in a control to the amount of radiolabeled polyamine incorporated diluted with polyamines present in physiological fluids. Polyamines can be first purified through a chromatography or extraction step in order to remove salts and other impurities that might alter the reaction. Either urine or erythrocytes can be used as the initial source of the polyamines. Spermidine levels in either fluid have been shown to reflect the body's cell loss component at the time of collection and assay. A polyamine assay kit with premeasured amounts of each chemical provides for the rapid and accurate assay of spermidine by an ordinary laboratory or medical technologist. Premeasured packets do away with the possible error of inaccurately calculated concentrations in any of the solutions.

The solutions can vary depending on the protein to be conjugated with the polyamines and a variety of buffer systems can be used. The system that is the cheapest and most foolproof is described herein. The content of putrescine, spermidine and spermine in biological fluids can be determined by a competitive radioenzymatic assay based on the addition of a known amount of transglutaminase activity. The assay can reliably detect 20 pmoles of putrescine, spermidine or spermine and is linear over the range 20–500 pmoles. Values obtained for total polyamine content of urine samples by this procedure are comparable to those obtained by an automated ion exchange method.

The procedure of this application has important advantages over the prior art. Accurate determinations in the past only allowed for 10–15 assays per day and required a highly skilled and dedicated technician to assure successful analysis and calculation of concentrations of polyamines. The premeasured ingredient kits will allow ease of assay and assure accuracy even when carried out by an unskilled technician. Rapid ability to assay multiple samples will make it possible to give rapid feedback to physicians related to the status of their patients. This is important to patients with cancer who are receiving highly cytotoxic agents who show they are not responding to chemotherapy by a lack of increase in polyamines in erythrocytes or urine.

In accordance with this invention, the amount of a polyamine in tissue or biological fluid is measured by a relatively fast and simple technique as outlined below. The polyamine may be any of the naturally occurring polyamines.

Putrescine ($NH_2-CH_2-CH_2-CH_2-CH_2-NH_2$) is present in all mammalian cells and the extracellular level (blood or urine) of putrescine is a marker of the fraction of total cells in the human body which are in cell cycle preparing to divide. Therefore, pathologies which normally have increased disease activity such as cancer, psoriasis, cystic fibrosis, and DMD have been shown to have elevated plasma and urine levels of putrescine. The extent of elevation is related to the extent of disease activity.

Spermidine ($NH_2-(CH_2)_3-NH-(CH_2)_4-NH_2$) has been shown to be present in highest concentrations in tissues during rapid growth such as embryogenesis, carcinogenesis and transformation. In erythrocytes, plasma, and urine, elevated spermidine has been correlated to the total cell loss factor of the body. Patients with metastatic cancer (carcinomas) were shown first to have elevated urinary spermidine which correlated with the high tumor cell loss factor characteristic of these tumors. Later, many investigators have substantiated that a greater than 2-fold increase in urinary spermidine within 24–72 hours prescribes a complete or partial response to therapy with a high degree of accuracy. This is important since there are no other early markers of response, and therapy usually involves the administration of cytotoxic drugs for at least 10 days. In addition, the putrescine and spermidine, in patients in remission, increase during relapse prior to other markers being available.

Figure 1:
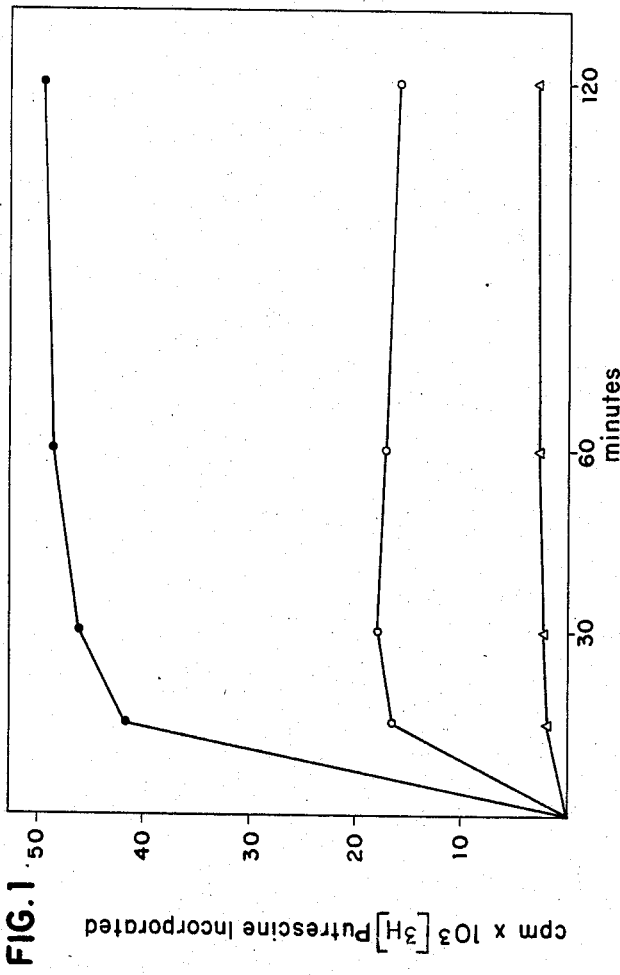
FIG. 1 illustrates the time-dependence of the transglutaminase reaction in the presence of limiting substrate concentration. Transglutaminase was incubated for the times indicated in the presence of 0.1 $\mu$M [$^3$H]-putrescine and 0.01 (open triangles), 0.10 (open circles) or 1.0 (closed circles) mg/ml dimethylated casein.

The ability of transglutaminase to incorporate polyamines into a covalent conjugate with protein is the basis for an assay procedure based on competition between radiolabeled polyamine and unlabeled polyamine-containing standards or samples as the enzyme's substrates. However, because the affinity of transglutaminase for amine-containing substrates is relatively low the assay reaction could not be conducted under saturating substrate conditions and yield the level of sensitivity required to measure the polyamine content of biological samples. Therefore, assay conditions were developed which would make the protein acceptor substrate ratelimiting and allow the reaction to be run to completion, the radioactive and unlabeled polyamine competing for the completion, the radioactive and unlabeled polyamine competing for the limited number of conjugation sites. The concentration of dimethylated casein was varied between 0.01 to 1 mg/ml and that of putrescine between 0.01 to 1.0 $\mu M$, and the time dependence of the reaction was examined. Representative data are shown in FIG. 1 for the experiments conducted with 0.1 $\mu M$ [$^3H$]putrescine, the concentration ultimately chosen for the routine assay. Increasing the amount of protein substrate added to the reaction resulted in an increase in conjugated putrescine. In all cases, the maximum incorporation was achieved by 30–60 minutes and was stable to another hour. Experiments examining the ability of unlabeled putrescine to compete under the conditions revealed that the inclusion of 0.1 mg/ml dimethylated casein resulted in maximum sensitivity of the assay.

Figure 2:
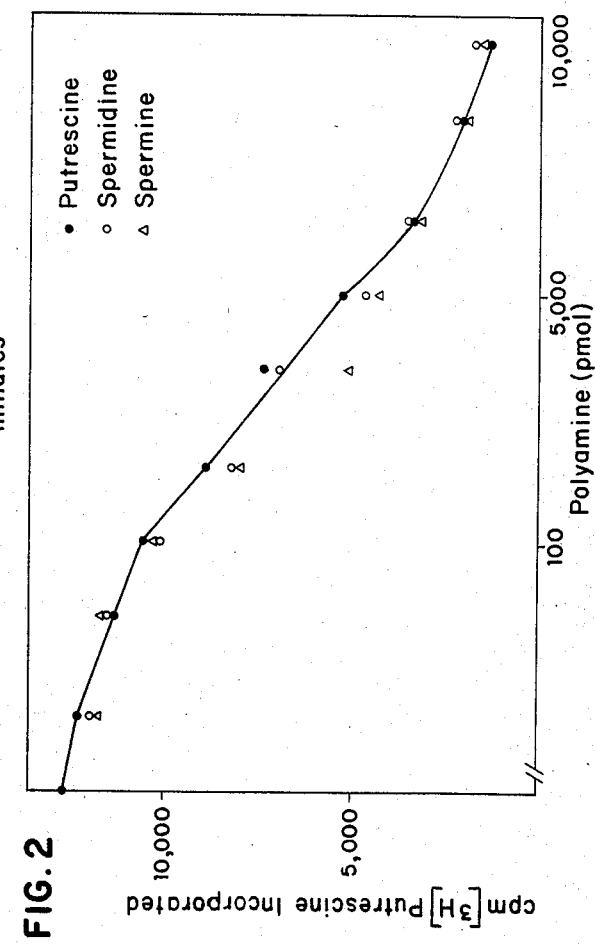
FIG. 2 is a standard curve of the transglutaminase-competition assay. Increasing amounts of unlabeled putrescine (closed circles), spermidine (open circles) or spermine (open triangles) were included in the transglutaminase reaction conducted as described except that 30 mM tris(hydroxymethyl)aminomethane HCl pH 8.0 was utilized as the reaction buffer.

FIG. 2 illustrates competition curves for putrescine, spermidine and spermine for the transglutaminase reaction. In the presence of 0.1 $\mu M$ [$^3H$]putrescine, all three of the unlabeled polyamines competed equally well, a significant inhibition of incorporation (1500–2000 cpm) observable in the presence of 50 pmoles of added polyamine and 50% displacement occurring at 800 pmoles.

Since the unprotonated form of the amine-containing substrate is the reactive component with the enzyme, the pH of the assay was varied to determine if the sensitivity could be increased. As shown in FIG. 3, raising the pH from 8.3 to 10.0 (reaction buffer glycine) increased both the amount of the radiolabeled putrescine incorporated and the steepness of the competition curve with the unlabeled added polyamine. At the elevated pH, a significant competition for incorporation (i.e., displacement of cpm > 10% of the total incorporated in the absence of unlabeled polyamine) was observed with 20 pmoles and 50% inhibition occurred at 200 pmoles. There is a linear relationship between the extent of competition and the amount of unlabeled polyamine added between 20–500 pmoles. Increasing the pH above 10 caused no further improvement. Consequently the standard conditions employed for the radioenzymatic assay of polyamines were incubation of 0.1 $\mu M$ [$^3H$]putrescine and 0.1 mg/ml dimethylated casein in 60 mM glycine, pH 10.

Because the polyamines are not the only components of biological fluids which can serve as substrates in the transglutaminase-catalyzed reaction with protein, the urine samples had to be partially purified before assay. The butanol extraction of the polyamines from the basic urine sample served to remove reactive amino acids, specifically lysine. Urine also contains alkylamines, such as ethylamine, which contain no acidic function and thus will coextract with the polyamines into the butanol. Therefore, the urine samples were chromatographed on Bio-Rex 70 to separate putrescine and the polyamines from the monoamine components. The polyamines are eluted by a buffer volume comparable to the initial urine volume and the eluates can be analyzed directly in the assay, eliminating the need for concentration by evaporation.

In order to ascertain the accuracy of the radioenzymatic method in quantitating polyamine levels in biological samples a series of human urine samples were analyzed both by ion exchange on an automated amino acid analyzer and by the transglutaminase-competition assay. As shown in Table 1, the results obtained by the two different methods are very similar.

The radioenzymatic method is simple to perform so that a large number of samples can be conducted in a single day. This method can also be used to quantitate individual values for putrescine, spermidine, and spermine in biological samples after prior fractionation of the amines by ion exchange column chromatography.

Rapid clean-up of urine can be done by absorbing the polyamines onto cation-exchange paper (eg. Whatman P81 paper). Putrescine and spermidine can be selectively eluted with an increasing NH₃ concentration. Therefore, the transglutaminase assay can now measure individually putrescine in its fraction, and spermidine after such separation. This would then allow for complete evaluation of tumor kinetics, i.e., growth fraction and cell loss fraction. In addition, it has been observed that human transplant patients show alterations in urinary polyamine profiles several days prior to a heart rejection episode. These alterations precede by several days the presence of a positive tissue biopsy of rejection, and are useful in implementing early elevated immunosuppressive therapy in these patients.

Other proteins can serve as substrates besides dimethylcasein. In fact, any protein with glutamine residues will work if the residues are exposed. Insulin is a known acceptor. Other common proteins can be made to be acceptors after oxidation. Therefore, an inexpensive acceptor substrate could be developed in all likelihood.

A rapid and accurate test for polyamines in physiological fluids will allow clinicians to assess disease activity and alterations in disease activity in a wide variety of pathologies. These data would be important in treatment as well as long term monitoring in diseases such as cancer.

TABLE 1

Comparison of Values for Polyamine Content of Urine Obtained By Automated Ion Exchange or Transglutaminase-Competition Assay[a]

| Sample No. | Polyamine Content | |
|---|---|---|
| | Ion Exchange | Transglutaminase |
| 1 | 27 | 36 |
| 2 | 46 | 49 |
| 3 | 61 | 62 |
| 4 | 51 | 46 |
| 5 | 46 | 37 |
| 6 | 32 | 32 |
| 7 | 37 | 40 |

[a]Urine samples were acidified and hydrolyzed overnight prior to analysis for polyamine content by an adapted automated amino acid analyzer or by the transglutaminase-competition radioenzymatic procedure. The values of total polyamine content as derived by the former method reflect the sum of the putrescine, spermidine and spermine content detected.

DETAILED DESCRIPTION OF THE INVENTION

The assay procedure is described below with reference to the polyamine putrescine. The same procedure can be used for other polyamines. The biological fluid containing the polyamine (putrescine) is first treated by known procedures such as butanol extraction [Raina, Acta. Phys. Scand. 60: Suppl. 218 (1963)] or adsorption on cation-exchange media to concentrate the putrescine and separate it from undesirable materials. The assay procedure includes the following steps:

(1) A standard amount of the putrescine concentrate to be assayed is mixed with an assay reagent containing a limiting amount of protein substrate, e.g. dimethylated casein, and a tracer amount of radiolabeled putrescine, eg. [³H]putrescine.

(2) Then an excess of the enzyme transglutaminase is added and the resulting solution incubated at 37° C. for about an hour. The transglutaminase causes the putrescine (both radiolabeled and nonlabeled) to become conjugated with the protein (dimethylated casein).

(3) Aliquots of the incubated solution are placed on instant thin layer chromatographic strips (ITLC) of silica gel supported on paper (Gelman) which had been treated with aqueous chlorinated alkanoic acid (e.g. trichloroacetic acid). On strips 1.5×10 cm in size, the chlorinated alkanoic acid is spotted between 2 and 4 cm and the aliquots of the enzyme reaction are spotted on top of that acid so that any radiolabeled putrescine incorporated into protein will precipitate on the strips. Ascending chromatography is carried out with dilute acid solution. Because the putrescine-dimethylcasein conjugate is insoluble in dilute acid solution, it does not migrate during the chromatography. The unincorporated radiolabeled putrescine is rapidly chromatographed to the top of the strips.

(4) The chromatographic strips are dried and cut into pieces containing the conjugate at or near the place of application of the incubated solution (between 2 and 4 cm). These pieces, containing both the radioactive and the "cold" conjugate, are submitted to scintillation counting which measures the total amounts of radiolabeled putrescine on the pieces.

The same procedure is simultaneously carried out with a standard amount of a putrescine solution of known concentration, and scintillation counts are made on the pieces of chromatographic strips.

From the radioactivity counts made on pieces of chromatographic strips which were treated with the putrescine concentrate to be assayed, and the counts made on strips treated with the standard putrescine solution, the amount of putrescine in the concentrate to be assayed can be calculated. Similar procedures can be carried out for assaying the other polyamine identified above.

EXAMPLE

The invention is disclosed in more detail by the following illustrative example which is typical of the assay method. Polyamines were extracted from urine by the addition of concentrated HCl to a final concentration of 0.1 N and the precipitated protein was removed by centrifugation at 20,000×g for 15 min. [¹⁴C]Cadaverine (0.1 μCi) was added to the acid supernatant to allow determination of the recovery rate of the polyamines through the extraction procedure. The samples were adjusted to 6 M HCl by addition of an equal volume of concentrated HCl and incubated overnight (16 h) at 100° C. to effect release of free polyamines from conjugated derivatives. The samples were made basic (greater than pH 11) by adjustment with 8.0 N NaOH, 1.2 g/5 ml of $Na_2SO_4/NA_3PO_4$ mixture (7:1, w:w) was added, and the polyamines were extracted by mixing for 10 min with ½ volume of butanol. The butanol layer was removed and the polyamines re-extracted into the aqueous phase by the addition of ½ volume 0.1 N HCl.

A weakly acidic carboxylic cation exchange resin, Bio-Rex 70 (100-200 mesh), was prepared by repeated mixing with 5 volumes of 0.1 N HCl until the pH of the aqueous phase was not altered by the addition of the resin. Columns (1×0.7 cm) were poured and washed with water until the eluate was at least pH 5. The samples extracted from butanol into 0.1 N HCl were adjusted to pH 5.5 by the addition of tris(hydroxymethyl)aminomethane, diluted 1:5 in distilled, deionized water (DDW), and applied to the column. After washing with 10 ml DDW, 80 ml of 20 mM glycine, 10 mM NaCl, pH 9.0, and 5 ml DDW, the polyamines were eluted from the resin with 3 ml 0.1 N HCl. The eluted sample was neutralized by the addition of tris(hydroxymethyl)aminomethane; standards were prepared in 0.1 N HCl and neutralized in a similar fashion. Recovery of the polyamines through the extraction procedure averaged 90-95%.

The polyamine content of samples and standards was measured by competition for the $Ca^{++}$-dependent incorporation of [$^3$H]putrescine into acid-precipitable protein catalyzed by guinea pig liver transglutaminase. The assay reaction mixture (50 μl) contained 60 mM glycine, pH 10.0, 30 mM NaCl, 10 mM 1,4-dithiothreitol, 5 mM $CaCl_2$, 0.1 mg/ml dimethylated casein, 0.1 μM [$^3$H]putrescine (0.55 μCi), and 20 μl of a known concentration of putrescine standard or 20 μl of a sample to be assayed for polyamines. The reaction was initiated by the addition of transglutaminase solution (10 μl), incubated 60 minutes at 37° C. Separation of the conjugated putrescine-protein product from radioactive free putrescine was achieved by rapid thin-layer chromatography on silica gel-impregnated glass fiber sheets. Chromatographic development requires only 10 minutes and circumvents the need for lengthy washing as used in filter paper procedures. Triplicate aliquots (35 μl) of the solution were spotted on 1.5×8 cm instant thin-layer chromatography strips at a site 1.5 cm above the bottom edge which had previously received 60 μl of 20% trichloroacetic acid. Ascending chromatography was immediately carried out in 5% trichloroacetic acid containing 0.2 M KCl. After the solvent front had reached the top of the strip (ca. 10 minutes), a 2.5-cm segment from 1.5 cm above the 1 cm below the origin was cut out, dried, and the segment counted in 6 ml of scintillation liquid (toluene/Omnifluor, New England Nuclear, Boston). In this chromatographic separation, the reaction product, [$^3$H]putrescine covalently conjugated to protein, which is insoluble in acid solution, remains at the origin while the free diamine moves with the solvent front. Analysis of entire chromatographed strips showed that, in the presence or absence of the protein substrate, more than 99.8% of the unconjugated putrescine moved away from the origin to the upper 2 cm of the strip. Reaction blank values, obtained by chromatography of reaction mixtures to which boiled transglutaminase had been added, routinely averaged 200-300 cpm. Recovery of conjugated protein product at the origin was slightly better than that achieved with the filter paper procedure.

I claim:

1. Method of determining the amount of naturally occurring organic polyamine in an aqueous solution to be assayed, which comprises (1) incubating a measured volume of said solution with a solution containing a protein with exposed glutamine residues and a small, known amount of radiolabeled polyamine, in the presence of transglutaminase, (2) placing aliquots of the incubated solution on thin layer chromatographic strips treated with aqueous acid, (3) treating said strips with dilute aqueous acid solution to cause ascending chromatography, (4) cutting from the strips the sections where the aliquots had been applied thereto, (5) counting the radioactive scintillations of said pieces, (6) carrying out steps (1) through (5) with the same volume of a standard solution containing a known amount of said polyamine, and (7) calculating the amount of polyamine in the solution to be assayed from the scintillation count made in the test procedure thereon in comparison to the scintillation count made in the test procedure conducted on the standard solution containing the known amount of said polyamine.

2. Method of claim 1 wherein the protein is dimethylated casein.

3. Method of claim 1 wherein the radiolabeled polyamine is labeled with $^3$H.

4. Method of claim 1 wherein the radiolabeled polyamine is labeled with $^{14}$C.

5. Method of claim 3 wherein the radiolabeled polyamine is [$^3$H]putrescine.

6. Method of claim 4 wherein the radiolabeled polyamine is [$^{14}$C]putrescine.

7. The method of claim 1 wherein the pH of the solution to be assayed and the pH of the standard solution are at least 10.

8. A method of determining the amount of naturally occurring organic polyamines in an aqueous solution to be assayed comprising:

incubating a measured volume of said solution with a solution containing a protein having exposed glutamine residues and a known amount of a radiolabeled polyamine, in the presence of a known amount of transglutaminase to form an incubated solution including naturally occurring polyamine conjugated to protein and free polyamine;

contacting an aliquot of the incubated solution with an agent capable of separating said conjugated polyamine from said free polyamine;

separating the conjugated polyamine from the free polyamine;

determining the amount of radiolabeled polyamine conjugated to said protein;

carrying out the the above process steps with the same volume of a standard solution containing a known amount of said polyamine; and calculating the amount of polyamine in the solution to be assayed by comparing the amount of radiolabeled polyamine conjugated to the protein in the standard solution to the amount of radiolabeled polyamine conjugated to the protein in the solution to be assayed.

9. The method of claim 8 wherein the amount of radiolabeled polyamine conjugated to the protein in both the standard solution and the solution to be assayed is determined by counting the radioactive scintillations in the conjugated polyamines.

10. The method of claim 8 wherein the conjugated polyamine is separated from the free polyamine by placing an aliquot of the incubated solution on a chromatographic strip and contacting the strip with a dilute acid to cause said separation.

11. The method of claim 10 including removing from the chromatographic strip the portion of the chromatographic strip containing the free polyamine prior to measuring the amount of radiolabeled polyamine conjugated to the protein on the remainder of the chromatographic strip.

12. The method of claim 8 wherein the concentration of the radiolabeled polyamine in the standard solution and in the solution to be assayed is 0.1 μM.

13. The method of claim 1 wherein the pH of the solution to be assayed and the pH of the standard solution are at least 10.

* * * * *